United States Patent [19]

Maurer

[11] 4,408,607
[45] Oct. 11, 1983

[54] CAPACITIVE ENERGY SOURCE AND CIRCUITRY FOR POWERING MEDICAL APPARATUS

[75] Inventor: Donald D. Maurer, Anoka, Minn.

[73] Assignee: EMPI, Inc., Fridley, Minn.

[21] Appl. No.: 253,308

[22] Filed: Apr. 13, 1981

[51] Int. Cl.³ .............................................. A61N 1/36
[52] U.S. Cl. ........................... 128/419 R; 128/419 PS
[58] Field of Search ......... 128/419 PS, 419 D, 419 R; 320/1, 2, 39, 40

[56] References Cited

U.S. PATENT DOCUMENTS

| | | | |
|---|---|---|---|
| 3,209,081 | 10/1961 | Ducote et al. | 128/419 PS |
| 3,258,013 | 6/1966 | Pruz | 128/419 D |
| 3,888,261 | 6/1975 | Maurer | 128/420 |
| 4,019,518 | 4/1977 | Maurer et al. | 128/419 |
| 4,096,866 | 6/1978 | Fischell | 128/419 PG |
| 4,275,739 | 6/1981 | Fischell | 128/419 PS |

OTHER PUBLICATIONS

NEC Electron, Inc. publication, "Super Capacitors".

Primary Examiner—William E. Kamm
Assistant Examiner—Mitchell J. Shein
Attorney, Agent, or Firm—Burd, Bartz & Gutenkauf

[57] ABSTRACT

An electric power supply operates to supply electrical energy to an electronic device implanted within a living body. The electric power supply has a capacitor which is used as the principal power source. A voltage regulator, overvoltage inhibitor, and a diode are cooperatively arranged to couple the capacitor with an induced voltage source used to charge the capacitor. The diode prevents the capacitor from discharging through the charging circuit when capacitor charging is not taking place. A regulator is used to control the electrical energy that flows to the electronic device. In one form of the electric power supply, a make-before-break switch unit is used to alternately connect the electric device with a charged capacitor or a battery power source so as to provide continuous electrical energy to the electronic device.

16 Claims, 4 Drawing Figures

CAPACITIVE ENERGY SOURCE AND CIRCUITRY FOR POWERING MEDICAL APPARATUS

TECHNICAL FIELD

This invention relates to the field of medical electronics, and particularly to apparatus for supplying power to devices surgically implanted in living bodies to continue in operation over extended intervals.

BACKGROUND OF THE INVENTION

Medical science has advanced to the point where it is possible to implant directly within living bodies electrical devices necessary or advantageous to the welfare of individual patients. A problem with such devices is how to supply the electrical energy necessary for their continued operation. The devices are, of course, designed to require a minimum of electrical energy, so that extended operation from batteries may be possible. Lithium batteries and other primary, non-rechargeable cells may be used, but they are expensive and require replacement of surgical procedures. Nickel-cadmium and other rechargeable batteries are also available, but have limited charge-recharge characteristics, require long intervals for recharging, and release gas during the charging process.

SUMMARY OF THE INVENTION

The present invention takes advantage of a new technology in capacitors by making a charged capacitor the principal power source for implantable devices, and providing for charging the capacitor from outside the living body. The very low current drain demanded by implantable devices, and the large capacitance and low leakage of the new capacitors, in acceptably small physical form, makes the use of charged capacitors as voltage sources feasible and practical, with the advantage that charging intervals for such capacitors are very much shorter than those for electro-chemical batteries. For some applications it may be necessary to isolate the device from the capacitor during the short charging interval. If the device in question cannot tolerate short-term power interruptions, an implanted backup power source may be provided in the form of an electro-chemical battery. The life of such a battery is greatly extended when it is only used for brief intervals during charging of a capacitor as a principal power source.

The invention includes implantable charging circuitry, and may also include means preventing the voltage rating of the capacitor from being exceeded, either by pressure responsive or other physical means, or by the electronic circuitry itself.

Various advantages and features of novelty which characterize the invention are pointed out with particularity in the claims annexed hereto and forming a part hereof. However, for a better understanding of the invention, its advantages, and objects attained by its use, reference should be had to the drawing which forms a further part hereof, and to the accompanying descriptive matter, in which there are illustrated and described certain embodiments of the invention.

BRIEF DESCRIPTION OF THE DRAWINGS

In the drawing, in which like reference numerals indicate corresponding parts throughout the several views.

DESCRIPTION OF THE PREFERRED EMBODIMENTS

Figure 1:
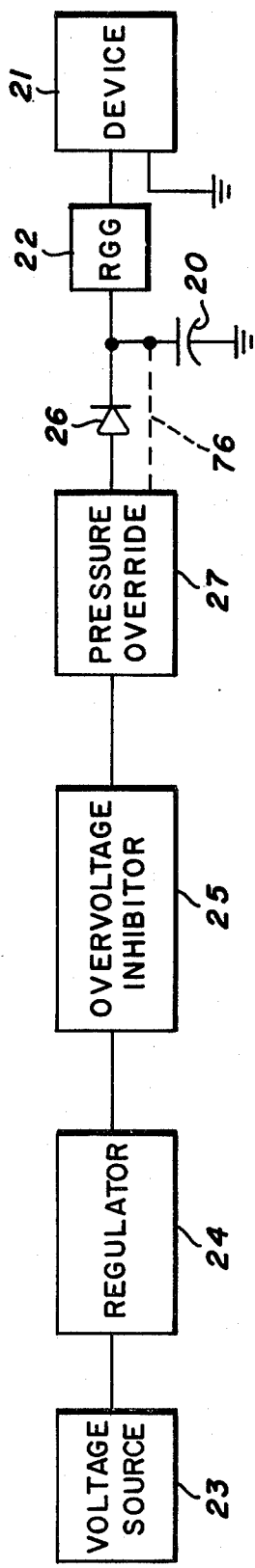
FIG. 1 is a block diagram of an embodiment of the invention.

Attention is first directed to FIG. 1 showing an implantable power supply according to the invention in block diagram. A capacitor 20, which is to act when charged as a voltage supply for an implanted device 21 through a voltage regulator 22, is arranged to be charged from an induced voltage source 23 through a regulator 24, an over-voltage inhibitor 25, and a diode 26. If desired, capacitor 20 may be encapsulated and a pressure override 27 may be actuated should the pressure in the capsule rise unduly. Diode 26 functions to prevent capacitor 20 from discharging through the charging circuitry when charging is not taking place.

Figure 2:
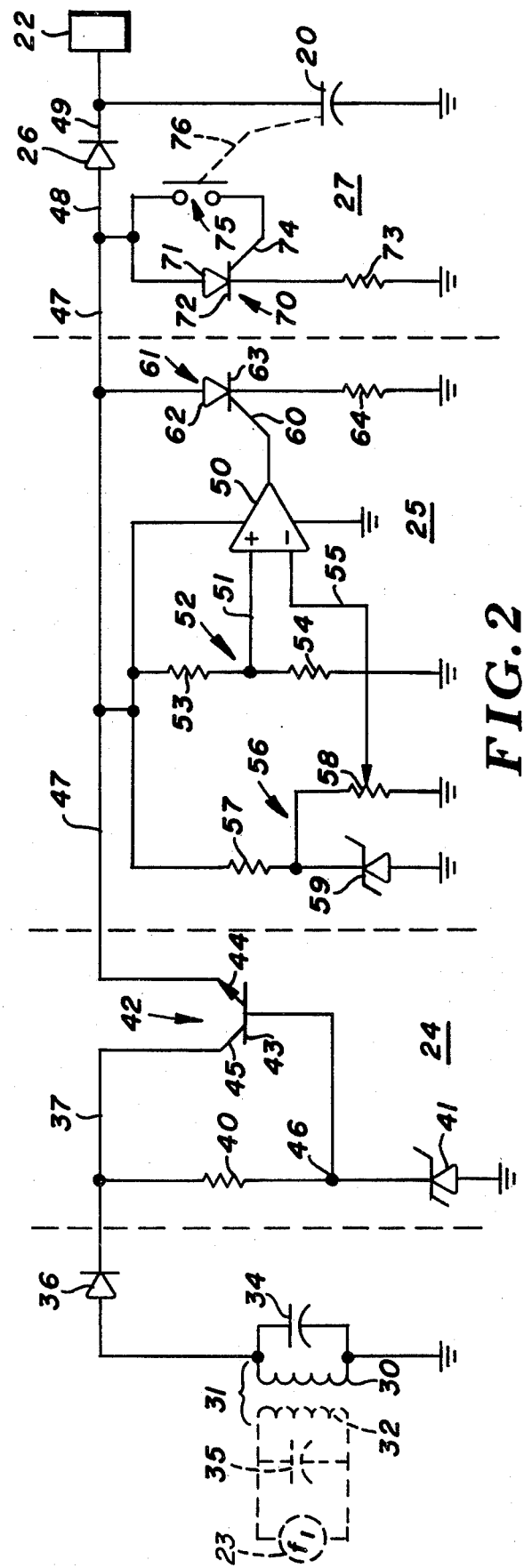
FIG. 2 is a circuit diagram of a first embodiment of an implantable power supply circuitry according to the invention.

FIG. 2 shows that voltage source 23 comprises a secondary winding 30 of a transformer 31, the removable primary winding 32 of which is external to the body in which the remaining components are implanted, for inductive energization of the charging circuitry from a source 23 of radio frequency energy of a chosen frequency. Windings 30 and 32 are preferably tuned by capacitors 34 and 35, respectively. Source 23 also includes a rectifying diode 36 so that the voltage on a conductor 37 is unidirectional.

Regulator 24 comprises a resistor 40, a Zener diode 41, a transistor 42 having a base 43, an emitter 44, and a collector 45. The junction point 46 between resistor 40 and Zener 41 is connected to base 43 so that the current flowing through the transistor from conductor 37 to an output conductor 47 remains constant.

Over-voltage inhibitor 25 comprises a voltage comparator 50 powered from conductor 47 and having a first input 51 from a voltage divider 52 made up of resistors 53 and 54, and a second input 55 from a voltage divider 56 made up of resistors 57 and 58, the latter being shunted by a Zener diode 59 to stabilize the second input to the comparator. The output of comparator 50 is supplied to the gate electrode 60 of a silicon controlled rectifier 61 having an anode 62 connected to conductor 47 and a cathode 63 grounded through a resistor 64. The output of inhibitor 25 is supplied to diode 26 through conductors 47 and 48, and thence to capacitor 20 and regulator 22 by conductor 49.

Pressure override 27 may comprise a silicon controlled rectifier 70 having an anode 71 connected to conductor 47, a cathode 72 connected to ground through a resistor 73, and a gating electrode 74 which may be connected to anode 71 when a normally open pressure switch 75 is closed by a mechanical connection 76 to the capsule of capacitor 20. Pressure override 27 is connected to diode 26 through a conductor 48.

When it is desired to charge capacitor 20, external primary winding 32 is apposed to implanted secondary winding 30 and source 23 is energized. An alternating voltage is induced in winding 30, rectified by diode 36, regulated to a level determined by Zener diode 41, and supplied through conductors 47 and 48 and diode 26 to capacitor 20, which remains connected to regulator 22 of device 21. After the expiration of the approved charging period, which may for example be on the order of 70 seconds, rather than several hours, as is the case for nickel-cadmium batteries, energization of primary winding 32 is interrupted, the voltage supplied to conductors 46 and 47 is terminated. The circuit is now ready for normal use of capacitor 20 as a power source, until the next charging period.

During use of capacitor 20 as a power source, the voltage on conductor 49 gradually decreases. When charging is undertaken, the voltage on conductor 48 must be greater than that of conductor 49 so that diode 26 can conduct the charging current. As charging continues, the voltage on conductor 48 must remain higher than that on conductor 49. It is understood that the voltage rating of capacitor 20 is chosen to be greater than the voltage which the capacitor is to supply as a power supply, but inadvertent overcharging of the capacitor is to be avoided. It is a characteristic of these capacitors that their rating voltage must not be exceeded, otherwise excessive out-gassing and even explosion will occur.

If the voltage on conductors 47 and 48 reaches a predetermined level less than the voltage rating of the capacitor, input 51 to comparator 50 becomes greater than input 55 and the comparator allows silicon controlled rectifier 61 to discharge, loading conductor 47 through resistor 64 so that its voltage drops and no further charging of the capacitor 20 takes place. Discharge of capacitor 20 through the silicon controlled rectifier is prevented by diode 26. This situation continues, by reason of "latching" of the silicon controlled rectifier, during any remaining excess of the charging interval. When source 23 is removed, the silicon controlled rectifier is de-energized and its latching is terminated, so that the charging circuit may return to its normal state.

Figure 3:
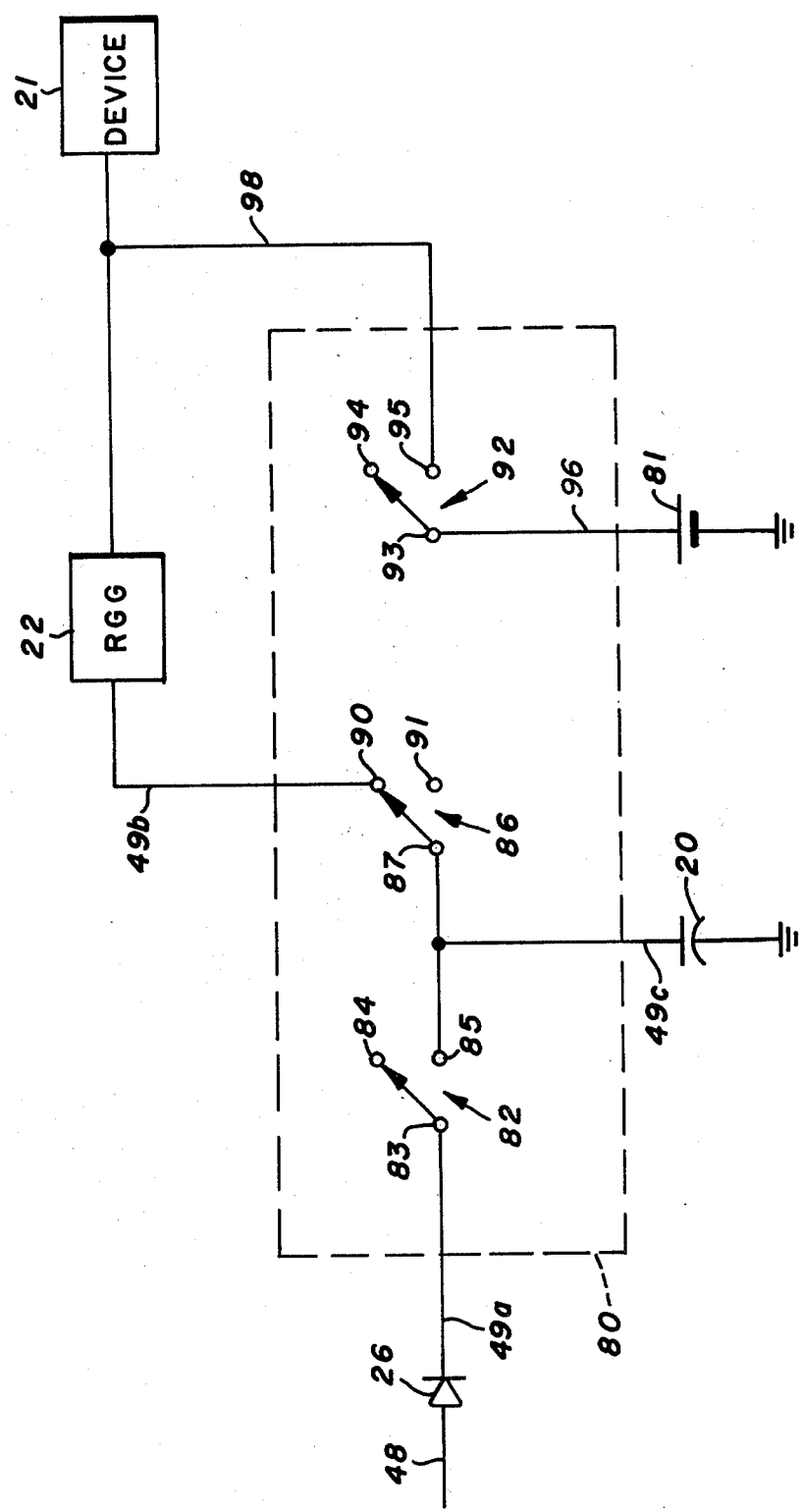
FIG. 3 shows a second embodiment of the invention adapted for use where the capacitor must be isolated from the powered device during charging, and yet no interruption of power to an implanted device can be tolerated.

FIG. 3 shows how the invention may be applied when the implanted device being powered cannot remain connected to said capacitor during charging, and cannot tolerate a power interruption. In the Figure, elements 20, 21, 22, and 26 are as previously described, but conductor 49 is interrupted by an implanted make-before-break switching arrangement 80 and appears as conductors 49a, 49b, and 49c. Also implanted is a lithium battery 81, which is to replace capacitor 20 as a power source during the charging period. More complete details of the switching arrangement 80 are given in FIG. 4, but FIG. 3 shows schematically the switching functions accomplished.

A first switch 82 has a movable contact 83, a normally closed contact 84, and a normally open contact 85. A second switch 86 has a movable contact 87, a normally closed contact 90 and a normally open contact 91. A third switch 92 has a movable contact 93, a normally closed contact 94, and a movable contact 95. Contact 83 is connected to diode 26 by conductor 49a. Contacts 85 and 87 are connected to capacitor 20 by conductor 49c. Contact 90 is connected to regulator 22 by conductor 49b. Contact 93 is connected to the positive pole of battery 81 by conductors 96 and 97, and contact 95 is connected to device 21 by conductor 98.

It is apparent that in the normal position of the switches, capacitor 20 is connected to supply power to regulator 22 through switch 86, battery 81 is isolated by switch 92, and rectifier 26 is isolated by switch 82. The switches are operated generally simultaneously, but in such a manner that switch 92 closes, to connect battery 81 to device 21, before switch 86 opens, to disconnect the capacitor from the device, so that battery 81 replaces capacitor 20 as a source of power for device 21 without any interruption. Switch 82 then connects the capacitor for charging, as described in connection with FIG. 2. Reverse operation of the switches disconnects the capacitor from the charging surface and connects it to the device before battery 81 is disconnected.

Figure 4:
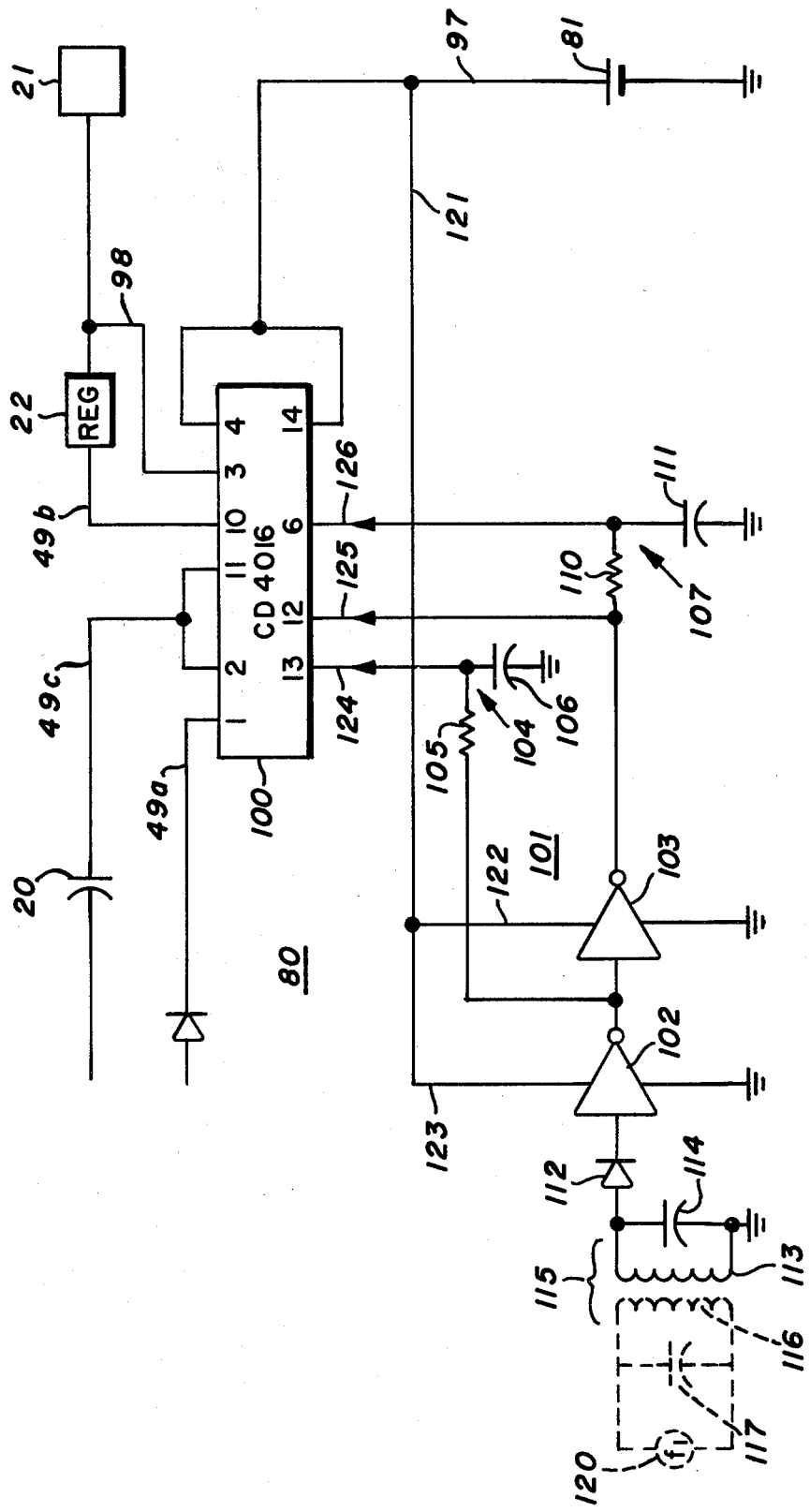
FIG. 4 is a fragmentary schematic of a detail of FIG. 3.

Reference should now be had to FIG. 4, which shows switching arrangement 80 in more detail. The actual switching functions are performed by a quad bilateral switch 100, preferably a CD 4016M/CD or 4016C. Switch 100 is controlled in its operation by circuit 101 including first and second operational amplifiers or Schmitt trigger inverters 102 and 103, a first timer circuit 104 including a resistor 105 and a capacitor 106, and a second timer circuit 107 including a resistor 110 and a capacitor 111, a diode 112, and the secondary winding 113, tuned by a capacitor 114, of a transformer 115. The primary winding 116 of transformer 115 is tuned by a capacitor 117. Winding 116 is outside the patient's body and is energized by a source 120 of radio frequency energy of a frequency different from that energizing transformer 31.

Schmitt trigger pulse shaping circuits 102 and 103 are energized from battery 81 through conductors 97, 121, 122, and 123 to supply control voltages to conductors 124, 125, and 126 relating to switch 100. The relation between FIGS. 3 and 4 is as follows. When a signal is supplied on conductor 124, conductor 49a is connected to conductor 49c, in the function of switch 82. When a signal is supplied on conductor 125, conductor 96 is connected to conductor 98, in the function of switch 92. When a signal is supplied on conductor 126, conductor 49c is disconnected from conductor 49b, in the function of switch 86.

When it is desired to charge capacitor 20, transformer winding 116 is apposed to secondary winding 133, and source 120 is energized. An induced voltage is supplied by winding 113, rectified by diode 112, and supplied to inverter 102, which supplies a negative-going pulse to timing circuit 104, where the pulse is delayed. The negative-going pulse from inverter 102 is also supplied without delay to inverter 103, which, in turn, supplies a positive-going pulse to conductor 125 directly, and to timing circuit 107, where it is delayed.

Accordingly, the signals on conductors 124 and 126 do not appear until after the signal has appeared on conductor 125, so that battery 81 is connected to device 21, by the function of switch 92, before the capacitor is disconnected from the device and connected to the charging circuit, the latter then being energized from transformer 31, as previously described.

At the end of the charging period source 120 is deenergized and the implanted circuit returns to its original condition, in which the now fully charged capacitor is connected to power the device and the battery is disconnected.

From the foregoing, it will be evident that the invention comprises apparatus whereby a charged capacitor may function as the power supply for a medical device implanted in a patient, and may be charged from a source external to the patient, and whereby an implanted battery may be substituted for the capacitor during charge intervals if the nature of the device requires uninterrupted energization.

Numerous characteristics and advantages of the invention have been set forth in the foregoing description, together with details of the structure and function of the invention, and the novel features thereof are pointed out in the appended claims. This disclosure, however, is illustrative only, and changes may be made in detail, especially in matters of shape, size, and arrangement of parts, within the principle of the invention, to the full extent indicated by the broad general meaning of the terms in which the appended claims are expressed.

The embodiments of the invention in which an exclusive property or privilege is claimed are defined as follows:

1. An electric power supply for providing electrical energy to an electrically operated medical device comprising:
capacitor means for accommodating an electric charge;
first means providing a regulated source of unidirectional electrical energy;
second means connecting said first means to said capacitor means for supplying charging current to said capacitor means at a first voltage which increases with charge in the capacitor means;
third means deriving from said first means a comparison second voltage of constant magnitude;
comparator means operative when said first voltage reaches a first value to reduce said first voltage to a second, lower value; and
voltage regulator means connected to said capacitor means and medical device to limit the voltage supplied to the medical device.

2. The power supply of claim 1 wherein: the third means and comparator means comprise a overvoltage inhibitor operable to prevent overcharging of the capacitor means.

3. The power supply of claim 1 including: means to encapsulate the capacitor means, and pressure override means operable to interrupt the charging current to the capacitor means when the pressure within the means to encapsulate the capacitor means increases.

4. The power supply of claim 3 wherein: the pressure override means includes a normally open pressure switch connected to the capacitor means.

5. The power supply of claim 1 including: battery means for providing a source of electrical power, and switch means for selectively connecting the capacitor means and battery means to said medical device, said switch means having make-before-break switch structure operable to maintain a continuous power supply to said medical device from either the capacitor means or the battery means.

6. The power supply of claim 5 wherein: the switch structure comprises a first switch operable to selectively connect and disconnect the capacitor means with the medical device and a second switch operable to selectively connect and disconnect the battery means from the medical device.

7. The power supply of claim 5 wherein: the switch structure includes a quad bilateral switch.

8. An electric power supply for providing electrical energy to an electrically operated medical device implanted in a biological body to supply electrical energy at a terminal within the body comprising:
an electro-chemical battery for providing an electric power source;
capacitor means for accommodating an electric charge;
first means providing a source of regulated unidirectional electrical energy inductively energizable from outside of the biological body for charging the capacitor means;
second means connecting said first means to said capacitor means for supplying charging current to said capacitor means at a first voltage which increases with charge in the capacitor means;
third means deriving from said first means a comparison second voltage of constant magnitude;
comparator means operative when said first voltage reaches a first value to reduce said first voltage to a second lower value; and
switch means movable from a first condition, in which said capacitor means is connected to said terminal providing electrical power thereto, and said battery is disconnected therefrom, to a second condition in which said battery is first connected to said terminal providing electrical power thereto and said capacitor means is then disconnected from said terminal and connected to said first means, said switch means operable to provide said terminal with a continuous supply of electrical power.

9. The power supply of claim 8 wherein: said switch means comprises a first switch operable to selectively connect and disconnect the capacitor means with said terminal, and a second switch operable to selectively connect and disconnect the battery with said terminal.

10. The power supply of claim 9 wherein: the switch means includes a quad bilateral switch.

11. An implantable power supply for a medical device comprising:
a capacitor;
first means providing a source of unidirectional electrical energy including a tuned transformer secondary and a diode;
second means including a translator and a Zener diode for charging said capacitor from said first means so that charging voltage supplied to said capacitor rises as the capacitor becomes charged; and
overvoltage inhibitor means operatively connected to said first means and capacitor operable to prevent overcharging of the capacitor, said overvoltage inhibitor means includes means responsive to the rise of said charging voltage above a first value for reducing said voltage to a second value and maintaining it at said second value until energization from said first means is interrupted.

12. The power supply of claim 11 including:
means encapsulating said capacitor; and
means responsive to rise of pressure in the means encapsulating said capacitor for reducing said voltage to a second value and maintaining it at said value until energization from said first means is interrupted.

13. The power supply of claim 12 wherein: the means responsive to rise of pressure includes a normally open pressure switch connected to the means encapsulating said capacitor.

14. The power supply of claim 11 including: battery means for providing a source of electrical power, and switch means for selectively connecting the capacitor and battery means to a medical device, said switch means having make-before-break switch structure operable to maintain a continuous power supply to said medical device from either said capacitor or the battery means.

15. The power supply of claim 14 wherein: the switch structure comprises a first switch operable to selectively connect and disconnect the capacitor with the medical device and a second switch operable to selectively connect and disconnect the battery from the medical device.

16. The power supply of claim 14 wherein: the switch structure includes a quad bilateral switch.

* * * * *

UNITED STATES PATENT AND TRADEMARK OFFICE
CERTIFICATE OF CORRECTION

PATENT NO. : 4,408,607
DATED : October 11, 1983
INVENTOR(S) : Donald D. Maurer

It is certified that error appears in the above-identified patent and that said Letters Patent is hereby corrected as shown below:

Column 1, line 23, "of" should be -- by --.

Column 4, line 42, "133" should be -- 113 --.

Column 6, claim 11, line 14, "includes" should be -- including --

Signed and Sealed this

Thirteenth Day of March 1984

[SEAL]

Attest:

GERALD J. MOSSINGHOFF

Attesting Officer    Commissioner of Patents and Trademarks